United States Patent
Pfrengle

[11] Patent Number: 5,462,944
[45] Date of Patent: Oct. 31, 1995

[54] FUNGICIDAL COMPOSITION AND METHOD OF COMBATING FUNGI

[75] Inventor: Waldemar F. A. Pfrengle, Seibersbach, Germany

[73] Assignee: Shell Research Limited, United Kingdom

[21] Appl. No.: 235,936

[22] Filed: May 2, 1994

[30] Foreign Application Priority Data

May 3, 1993 [EP] European Pat. Off. ............. 93107131

[51] Int. Cl.$^6$ ................ A61K 31/505; C07D 405/12

[52] U.S. Cl. ............. 514/275; 514/272; 544/230; 544/298; 544/330; 544/332

[58] Field of Search ................. 514/272, 275; 544/230, 320, 330, 332, 298

[56] References Cited

FOREIGN PATENT DOCUMENTS

| | | |
|---|---|---|
| 281842 | 9/1988 | European Pat. Off. . |
| 349247 | 1/1990 | European Pat. Off. . |
| 413223 | 2/1991 | European Pat. Off. . |
| 278352 | 4/1991 | European Pat. Off. . |
| WO92/16518 | 10/1992 | WIPO . |
| WO93/19050 | 9/1993 | WIPO . |

OTHER PUBLICATIONS

Chemical Abstract vol. 100: 107483, 1988.
Chemical Abstract vol. 96: 205499, 1982.
Bombardt, Paul A. et al., "Liquid Chromatographic Determination of Guanadrel in Laboratory Animal Diet as the Fluorescent Acetylacetone Derivative", Analytical Chemistry, vol. 54, No. 7, pp. 1087–1090, 1982.
Kaiser, D. et al., "Gas Chromatographic Determination of Guanadrel in Plasma and Urine", Journal of Chromatography–Biomedical Applications, vol. 434, No. 1. pp. 135–143, 1988.
Omichi, Kaoru et al., "Linkage Position Analysis of Pyridylamino–Disaccharides by HPLC of Fluorogenic Smith Degradation Products", Journal of Biochemistry, vol. 115, No. 3, pp. 429–434, Mar. 1994.

Primary Examiner—Mukund J. Shah
Assistant Examiner—Yogendra N. Gupta

[57] ABSTRACT

Spiroheterocyclic compounds having fungicidal activity are disclosed having the formula:

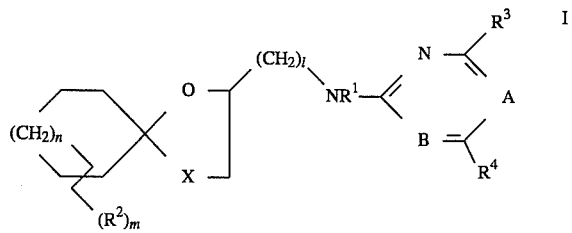

in which X is O or $CH_2$; $R^1$ is hydrogen or optionally substituted alkyl, cycloalkyl, haloalkyl, alkenyl, alkynyl, aryl or aralkyl; $R^2$ is optionally substituted alkyl, cycloalkyl, cycloalkylalkyl, alkoxy, alkoxyalkyl, aryl or aryloxy, or together with the ring to which they are attached represents a polycyclic hydrocarbyl group; A and B both represent nitrogen, or A represnts the gorup $CR^5$ and B represents nitrogen or $CR^6$; l is an integer from 1 to 3; m is zero or an integer from 1 to 6; and n represents zero or an integer from 1 to 3.

16 Claims, No Drawings

FUNGICIDAL COMPOSITION AND METHOD OF COMBATING FUNGI

The present invention relates to certain new spiroheterocyclic compounds having fungicidal properties, processes for the preparation of these compounds, fungicidal compositions containing the compounds and the use of the compounds as fungicides for the control of phytopathogenic fungi.

In EP 281842, EP 349247 and EP 413223 fungicidal spiroheterocyclic compounds have been described. These known compounds contain a substituted cyclohexyl ring in spiro conjunction with a substituted heterocyclic five or six membered ring. The substituents of the cyclohexyl ring are usually (substituted) (branched) alkyl or phenyl groups. The substituents of the heterocyclic ring are usually (substituted) (cyclo)alkyl- or dialkyl-amino-methyl or dialkyl-amino-polymethyl groups, including alkylene-amino-methyl or alkylene-amino-polymethyl groups. Other fungicidal spiroheterocyclic compounds have been described in EP 278352 and WO 92/16518.

It has now been found that certain new spiroheterocyclic compounds show excellent fungicidal activity against certain phytopathogenic fungi, for instance against *Plasmopora viticola, Botrytis cinerea, Erysiphe graminis, Pseudocercosporella herpotrichoides, Rhizoctonia solani* and *Venturia inaequalis*.

The present invention therefore relates to compounds of the general formula I

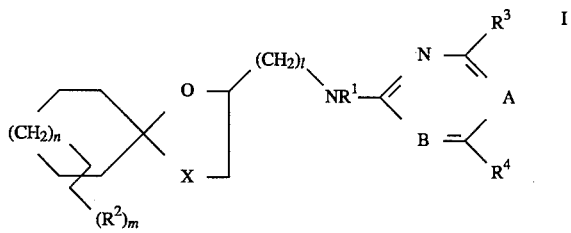

in which

X represents O or $CH_2$, $R^1$ represents a hydrogen atom or an optionally substituted alkyl, cycloalkyl, haloalkyl, alkenyl, alkynyl, aryl or aralkyl group, $R^2$ or each $R^2$ independently represents an optionally substituted alkyl, cycloalkyl, cycloalkylalkyl, alkoxy, alkoxyalkyl, aryl or aryloxy group, or $R^2$ or each $R^2$, together with the ring to which they are attached, represents a polycyclic hydrocarbyl group, A and B both represent a nitrogen atom, or A represents a group $CR^5$ and B represents a nitrogen atom or a group $CR^6$, $R^3$, $R^4$, $R^5$ and $R^6$ each independently represent a hydrogen or halogen atom, a hydroxy or cyano group or an optionally substituted alkyl, alkenyl, alkynyl, haloalkyl, alkoxyalkyl, aralkyl, aryl, alkylamino, alkenylamino, alkylthio, alkoxy, alkenoxy or alkynoxy group, l represents an integer from 1 to 3, m represents zero or an integer from 1 to 6, and n represents zero or an integer from 1 to 3.

The invention especially relates to compounds of the general formula I in which any alkyl, alkenyl, alkynyl part of any of the substituents $R^1$ to $R^6$ contains up to 12 carbon atoms, preferably up to 10 carbon atoms, more preferably up to 8 carbon atoms, any cycloalkyl part of any of the substituents $R^1$ to $R^6$ contains from 3 to 10 carbon atoms, preferably from 3 to 8 carbon atoms, more preferably from 3 to 6 carbon atoms, any alkylene chain contains from 3 to 6 chain members, and any aryl part of any of the substituents $R^1$ to $R^6$ contains 6, 10 or 14 carbon atoms, preferably 6 or 10 carbon atoms, and in which each optionally substituted group independently is substituted by one or more halogen atoms or nitro, cyano, alkyl, preferably $C_{1-6}$ alkyl, cycloalkyl, preferably $C_{3-6}$ cycloalkyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, optionally substituted amino, acyl, alkoxycarbonyl, preferably $C_{1-6}$ alkoxycarbonyl, carboxyl, phenyl or halo- or dihalo-phenyl groups. Optionally substituted amino groups include amino groups substituted by one or two groups selected from alkyl, aryl, cycloalkyl, cycloalkylalkyl and aralkyl groups, in particular alkylamino, dialkylamino, arylamino, haloarylamino and benzylamino. Any acyl group includes formyl, optionally substituted alkyl carbonyl and optionally substituted aryl carbonyl groups. Any alkyl, alkenyl or alkynyl group may be linear or branched. Preferred alkyl substituents are at least methyl, ethyl, propyl and butyl. A halogen atom suitably denotes a fluorine, chlorine or bromine atom.

The invention especially relates to compounds of the general formula I, in which X represents O.

The invention further especially relates to compounds of the general formula I in which $R^1$ represents a hydrogen atom, a $C_{1-6}$ alkyl, $C_{3-6}$ cycloalkyl, $C_{2-6}$ alkenyl, $C_{2-6}$ alkynyl, phenyl or benzyl group, each group optionally substituted by one or more halogen atoms, especially chlorine and/or fluorine atoms, or $C_{1-4}$ alkyl, $C_{1-4}$ haloalkyl, $C_{1-4}$ alkoxy, $C_{1-4}$ alkylamino, $C_{1-4}$ dialkylamino or phenylamino groups. $R^1$ preferably represents a hydrogen atom or a methyl or ethyl group optionally substituted by up to three chlorine or fluorine atoms, an ethenyl, propenyl or propynyl group or a phenyl or benzyl group.

The invention also especially relates to compounds of the general formula I in which $R^2$ or each $R^2$ represents a $C_{1-10}$ alkyl, $C_{3-6}$ cycloalkyl, $C_{3-8}$ cycloalkyl-$C_{1-6}$ alkyl, $C_{1-6}$ alkoxy, $C_{1-10}$ alkoxy-$C_{1-6}$ alkyl or phenyl group, or $R^2$ or each $R^2$ together with the ring to which they are attached, represents a $C_{7-20}$ polycyclic group, preferably a $C_{8-12}$ bicyclic, $C_{9-14}$ tricyclic or $C_{9-16}$ quadricyclic hydrocarbyl group, preferably a saturated hydrocarbyl group, each of the above groups optionally substituted by one or more halogen atoms, especially chlorine and/or fluorine atoms, or $C_{1-4}$ alkyl, $C_{1-4}$ haloalkyl or $C_{1-4}$ alkoxy groups. $R^2$ preferably represents a $C_{1-8}$ alkyl group, especially a branched alkyl group. Especially suitable are secondary and tertiary alkyl groups as secondary butyl, tertiary butyl and tertiary amyl groups. More preferably $R^2$ represents a t-butyl or t-amyl group. The invention also especially relates to compounds of the general formula I in which m represents an integer from 1 to 4, preferably 1 or 2, more preferably 1. The group or groups $R^2$ are preferably attached to the positions 3, 4 and/or 5 of the cyclohexyl ring, especially a cyclohexyl ring, more preferably to the 4-position.

The invention further especially relates to compounds of the general formula I in which A and B both represent a nitrogen atom or A represents a group $CR^5$ and B represents a nitrogen atom. Preferably A represents a group $CR^5$ and B represents a nitrogen atom.

The invention further especially relates to compounds of the general formula I in which $R^3$, $R^4$, $R^5$ and $R^6$ each independently represent a hydrogen or halogen atom, a hydroxy group or an optionally substituted $C_{1-8}$ alkyl, $C_{1-6}$ alkenyl, $C_{1-6}$ haloalkyl, benzyl, phenyl or $C_{1-6}$ alkoxy group, each group optionally substituted by one or more halogen atoms, especially chlorine and/or fluorine atoms, or $C_{1-4}$ alkyl, $C_{1-4}$ haloalkyl, $C_{1-4}$ alkoxy, $C_{1-4}$ alkylamino, $C_{1-4}$ dialkylamino or phenylamino groups. $R^3$ and $R^4$ each independently preferably represent a hydrogen or halogen atom, especially a chlorine or fluorine atom, a hydroxy group or a methyl, ethyl, propyl, butyl, pentyl, hexyl, phenyl, methoxy or ethoxy group, each group optionally substituted by up to five chlorine or fluorine atoms, especially three chlorine or fluorine atoms. $R^5$ and $R^6$ each independently preferably represent a hydrogen or halogen atom, especially a chlorine or fluorine atom, or a methyl, ethyl, propyl, methoxy or ethoxy group, each group optionally substituted by up to three chlorine or fluorine atoms.

The invention especially relates to compounds of the general formula I in which l represents 1 and n represents 1.

A particular preferred sub-group of compounds of the general formula I is that in which $R^1$ represents a hydrogen atom. Another preferred sub-group of compounds of the general formula I is that in which $R^2$ or each $R^2$ independently represents a methyl, propyl, especially i-propyl, butyl, especially t-butyl, pentyl, especially t-amyl, cyclohexyl or phenyl group, or in the case of a polycyclic structure, two groups R represent a tetra- or penta-methylene group. Further preferred sub-groups of the general formula I are those in which $R^3$ and $R^4$ each independently represent a hydrogen or chlorine atom or a methyl, butyl, especially i-butyl, or methoxy group, and $R^5$ and $R^6$ each independently represent a hydrogen atom or a trifluoromethyl group.

The present invention further provides a process for the preparation of compounds of the general formula I as defined hereinbefore in which X represents O, which process comprises reacting a compound of the general formula II

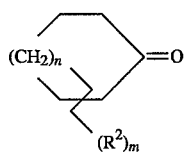

in which $R^2$, n and m are as defined hereinbefore, with a compound of the general formula III

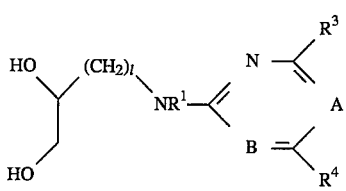

in which $R^1$, $R^3$, $R^4$, A, B and l are as defined hereinbefore, as well as a process for the preparation of compounds of the general formula I as defined hereinbefore and in which X represents O or $CH_2$, which process comprises reaction of a compound of the general formula IV

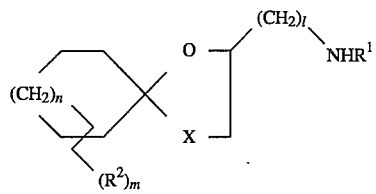

in which $R^1$, $R^2$, l, m and n are as defined hereinbefore, with a compound of the general formula V

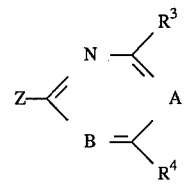

in which $R^3$, $R^4$, A and B are as defined hereinbefore and Z represents a leaving group, or, optionally, in the case A represents a group $CR^5$ and B represents N, by reaction of a compound of the general formula IV with a compound of the general formula VI

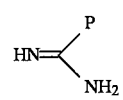

in which P represents a leaving group, followed by reaction with a compound of the general formula VII

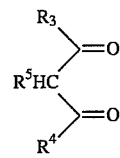

in which $R^3$, $R^4$ and $R^5$ are as defined hereinbefore, while in the case that $R^1$ represents a hydrogen atom, this hydrogen atom may be exchanged by another substituent within the definition of $R^1$ by reaction with a suitable alkylating agent.

It will be appreciated that between the above indicated reaction steps additional chemical modification can be made to the compounds obtained, e.g. introduction or amendment of certain substituents in the cycloalkyl or heteroaromatic ring.

The starting compounds with the general formula II are known in the literature, and many of them are commercially available.

Compounds of the general formula III are new compounds. These compounds form part of the present invention. These compounds may be prepared by oxidation of an alkene of the general formula VIII

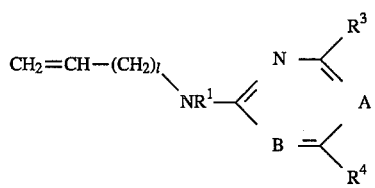

in which $R^1$, $R^3$, $R^4$, A, B and l are as defined hereinbefore with a suitable oxidant, for instance with potassium permanganate or, especially, osmium tetroxide, especially a catalytic amount thereof together with a regeneration reagent. The alkenes of the general formula VIII may be prepared by reaction of a (substituted) alkenylamine with a compound of the general formula V as defined above, or by reaction of a (substituted) alkenylamine and a compound of the general formula VI as defined above, followed by reaction with a compound of the general formula VII as defined above. Compounds of the general formulas VI and VII are known in the literature, or can be prepared in analogous ways. Alternatively, compounds of the general formula III can be prepared by reaction of a compound of the general formula V with a compound of the general formula XI

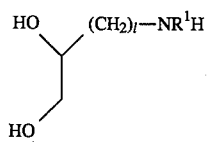

in which $R^1$ and 1 are as defined hereinbefore.

Compounds of the general formula IV can be prepared by reaction of a compound of the general formula X

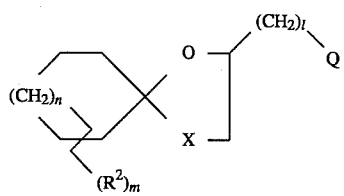

in which $R^2$, X, l, m and n are as defined hereinbefore and Q represents a leaving group, with a compound of the formula $R^1\text{-}NH_2$, in which $R^1$ represents a hydrogen atom or an optionally substituted alkyl, cycloalkyl, haloalkyl, alkenyl, alkynyl, aryl or aralkyl group. Compounds of the general formula X are known from the literature, see for example EP 281842, EP 413223 and EP 278352.

A leaving group is any group that, under the reaction conditions appropriate for the reaction involved, will cleave from the starting material, thus enabling substitution at that specific site. The leaving group Z may suitably be a halogen atom, for example a bromine atom or, especially, a chlorine atom, an alkoxy group, suitably $C_{1-4}$ alkoxy, especially methoxy, an alkyl- or arylsulphonium group, especially a $C_{1-6}$ alkyl-, phenyl- or tolylsulphonium group, or an alkyl- or aryl-sulphonic acid group, especially a $C_{1-6}$ alkyl-, phenyl- or tolyl-sulphonic acid group. The leaving group P is suitably an alkoxy or alkylthio group, suitably a $C_{1-4}$ alkoxy or $C_{1-4}$ alkylthio group, especially a methoxy or methylthio group. The leaving group Q may suitably be a halogen atom, for example a bromine atom or, especially, a chlorine atom, an alkyl- or aryl-sulphonium group, especially a $C_{1-6}$ alkyl-, phenyl- or tolyl-sulphonium group, or an alkyl- or arylsulphonic acid group, especially a $C_{1-6}$ alkyl-, phenyl- or tolyl-sulphonic acid group.

The process of the present invention in which the heterocyclic spirocompound is formed is suitably carried out in the presence of an organic solvent, for example an alkane, an aromatic solvent, a chlorinated hydrocarbon or an ether. Especially suitable are those organic solvents which form an azeotrope with water, such as benzene, toluene, chloroform etc.

The process is suitably carried out at a temperature in the range of 0° to 150° C., especially between 40° and 120 ° C., preferably at the reflux temperature of the solvent, and suitably in the presence of a acid.

Suitably the reaction is carried out using substantially equimolar amounts of the reactants. However, it can be expedient to use one reactant in excess.

The process of the present invention in which a compound of the general formula IV is reacted with a compound of the general formula V or VI may be carried out in the presence or absence of an organic solvent, for example an alcohol or a formamide. Especially suitable are polar organic solvents as dimethylsulfoxide and hexamethylphosphortriamide.

The reaction is suitably carried out at a temperature in the range of 50° to 250° C., especially between 90° and 210 ° C.

The reaction of the present invention in which the intermediate formed after the reaction of a compound of the general formula IV with a compound of the general formula VI is reacted with a compound of the general formula VII is preferably carried out in the presence of an organic solvent, for example an alkane, an aromatic solvent, a chlorinated hydrocarbon or an ether. Especially suitable are those organic solvents which form an azeotrope with water, such as benzene, toluene, chloroform etc.

The process is suitably carried out at a temperature in the range of 0° to 150° C., especially between 40° and 120 ° C., preferably at the reflux temperature of the solvent, and suitably in the presence of a acid.

The invention also provides fungicidal compositions comprising at least one of the compounds according to general formula I or an acid addition salt thereof, as well as methods of combating fungi at a locus comprising treatment of the locus with a compound of formula I or an acid addition salt thereof as defined hereinbefore, or with a composition as defined in this specification. The locus to be treated especially comprises plants subject to or subjected to fungal attack, seeds of such plants or the medium in which the plants are growing or are to be grown.

The fungicidal composition comprises a carrier and, as active ingredient, a compound of the general formula I or an acid addition salt thereof.

A method of making such a composition is also provided, which comprises bringing a compound of the general formula I as defined above or an acid addition salt thereof into association with at least one carrier. Such a composition may contain a single compound or a mixture of several compounds of the present invention. It is also envisaged that different isomers or mixtures of isomers may have different levels or spectra of activity and thus compositions may comprise individual isomers or mixtures of isomers.

The invention further relates to the use as a fungicide of a compound of formula I as defined hereinbefore or a composition as defined hereinbefore.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl tsobutyl ketone and cyclohexanone; ethers; aromatic or araliphattc hydrocarbons, for example benzene, toluene and xylene; petroleum fractions, for example, kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilizers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The present invention still further provides the use as a fungicide of a compound of the general formula I as defined above or a composition as defined above.

The present invention is of wide applicability in the protection of crop plants against fungal attack. Typical crops which may be protected include cereals, especially wheat and barley, rice, vines, potatoes, tomatoes, top fruit, especially apples, and cucumber. The duration of protection is normally dependent on the individual compound selected, and also a variety of external factors, such as climate, whose impact is normally mitigated by the use of a suitable formulation. The compounds of the present invention are especially suitable to combat *Erysiphe graminis* in cereals.

The invention is further illustrated by the following examples.

EXAMPLE 1

8-t-Butyl-2-(4,6-dimethylpyrimid-2-ylaminomethyl)-1,4-dioxaspiro-(4,5)decane (i) Preparation of 1-(4,6-dimethylpyrimid-2-ylamino)-prop-2-ene 4,6-dimethyl-2-methylsulfonylpyrimidine (93.0 g, 0.5 mol) and arallylamine (250 ml) were heated to reflux for 1 hour. Excess allylamine was distilled off and water (800 ml) was added. The crystalline product was filtrated and washed with water. Drying in vacuum yields 76.2 g of yellowish crystals (m.p. 62°–63° C.).

(ii) Preparation of 3-(4,6-dimethylpyrimid-2-ylamino)propane-1,2-diol

N-methylmorpholine-N-oxide (64.0 g, 0.47 mol) and osmiumtetroxide (0.7 g, 2.75 mmol) were dissolved in a mixture of 180 ml water and 100 ml acetone. 1-(4,6-dimethylpyrimid-2-ylamino) -prop-2-ene (73.5 g, 0.45 mol)

in 100 ml acetone was added over a period of 15 minutes. The mixture was stirred at room temperature for 1 hour and then warmed to 50° C. for 2 hours. 10 ml aqueous saturated sodiumhydrogensulphite was then added together with 40 g of diatomaceous earth. After filtration the reaction mixture was evaporated to dryness and the residue extracted with dioxane/ethanol 2:1 (700 ml). Filtration from insoluble material and concentration of the solution in vacuum caused crystallisation of the product. Addition of toluene completed product precipitation, which was isolated by filtration (83 g, m.p. 124°–127° C.).

(iii) Preparation of 8-t-butyl-2-(4,6-dimethylpyrimid-2-ylamino-methyl)-1,4-dioxaspiro(4,5)decane 3-(4,6-dimethylpyrimid-2-ylamino)-propane-1,2-diol (4.0 g, 20 mmol), 4-t-butyl cyclohexanone (3.08 g, 20 mmol) and p-toluenesulfonic acid (4.3 g, 22 mmol) in 50 ml benzene were refluxed on a water trap for 1 hour. The reaction mixture was washed twice with saturated aqueous sodium carbonate (50 ml), dried with magnesium sulphate and evaporated in vacuum. Kugelrohr- distillation of the resulting oil yielded 6.0 g of a colourless oil (b.p. 200° C./0.2 mbar) which was recrystallised from light petroleum to yield 5.0 g of colourless crystals (m.p. 121°–124° C.). GLC-MS analysis indicates an approximately 1:1 mixture of diastereoisomers (cis/trans).

EXAMPLE 2

8-t-Butyl-2-(4,6-dimethoxy pyrimid-2-ylamino-methyl)-1,4-dioxaspiro(4,5)decane

(i) Preparation of 8-t-butyl-2-(phthalimidomethyl)-1,4-dioxaspiro(4,5)decane A mixture of 8-t-butyl-2-chloromethyl-1,4-dioxaspiro(4,5)decane (10 g, 40 mmol) (prepared as described in EP 281842; see also the references cited in this document for related compounds), potassium phthalimide (8.9 g, 48 mmol) and a catalytic amount of tetra-n-butyl ammonium iodide in DMF (80 ml) were heated to 120° C. for 3 hours. Additional potassium phthalimide (2.8 g, 16 mmol) was then added and heating was continued for 6 hours. The solvent was then evaporated in vacuo and toluene (150 ml) was added. After filtration from insoluble material the organic phase was washed two times with brine (100 ml), dried (MgSO$_4$) and evaporated in vacuo. The resulting residue (22 g) was purified by flash chromatography on silica (toluene/ ethylacetate 3:1) yielding the title compound as light yellow crystals (14.5 g, Fp. 97°–115° C.).

(ii) Preparation of 8-t-butyl-2-aminomethyl-1,4-dioxaspiro(4,5)decane

To a warm (50° C.) solution of 8-t-butyl-2-(phthalimidomethyl)1,4-dioxaspiro (4,5)decane (12.5 g, 35 mmol) in ethanol (100 ml) was added hydrazine hydrate (3.6 g, 72 mmol). The reaction mixture was kept at 50° C. for 1 hour. Light petroleum 200 ml was added and insoluble material was filtered off. The solvent was evaporated in vacuo. The residue was dissolved in toluene (100 ml) washed with brine (100 ml) and dried (MgSO$_4$). Evaporation of the solvent yielded the title compound as a yellow oil (7.2 g). GC analysis indicated the compound as existing as a mixture of two diastereoisomers (cis, cis and cis, trans) in a ratio of 48:52. The NMR spectra are in agreement with the assigned structure.

(iii) Preparation of 8-t-butyl-2-(4,6-dimethoxy pyrimid-2-ylaminomethyl)-1,4-dioxaspiro(4,5)decane 8-t-butyl-2-aminomethyl-1,4-dioxaspiro(4,5)decane (3.3 g, 14.5 mmol), 4,6-dimethoxy-2-methylsulfonyl-pyrimidine (3.16 g, 14.5 mmol) and potassium carbonate (2.76 g, 20 mmol) were heated to 160° C. for 1 hour. The reaction mixture was then extracted with toluene and the concentrated extracts purified by flash chromatography using a 3:1 mixture of toluene and ethylacetate. 3.5 g of a faint yellow oil was obtained which crystallised on standing. NMR analysis indicated the product being a mixture of diastereoisomers. M.p.: 76°–106° C.

Elemental analysis: Calc. C: 62.55 H: 8.55 N: 11.50
Found C: 62.75 H: 8.42 N: 10.79

EXAMPLES 3 TO 55

By processes similar to those described in Examples 1 and 2 above, further compounds according to the invention were prepared as detailed in Table 1 below. In this table, the compounds are identified by reference to formula I.

TABLE I

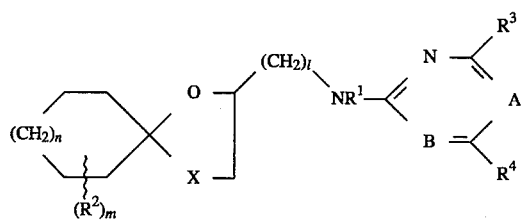

| Ex. No. | $R^1$ | $R^2$ | $R^3$ | $R^4$ | X | A | B | l | m | n |
|---|---|---|---|---|---|---|---|---|---|---|
| 1. | H | 4-t-C$_4$H$_9$ | —CH$_3$ | —CH$_3$ | O | —CH— | —N— | 1 | 1 | 1 |
| 2. | H | 4-t-C$_4$H$_9$ | —OCH$_3$ | —OCH$_3$ | O | —CH— | —N— | 1 | 1 | 1 |
| 3. | H | 4-i-C$_3$H$_7$ | —CH$_3$ | —CH$_3$ | O | —CH— | —N— | 1 | 1 | 1 |
| 4. | H | 4-C$_6$H$_5$ | —CH$_3$ | —CH$_3$ | O | —CH— | —N— | 1 | 1 | 1 |
| 5. | H | 3,5-(CH$_3$)$_2$ | —CH$_3$ | —CH$_3$ | O | —CH— | —N— | 1 | 2 | 1 |
| 6. | H | 4-t-C$_5$H$_{11}$ | —CH$_3$ | —CH$_3$ | O | —CH— | —N— | 1 | 1 | 1 |

TABLE I-continued

I

| Ex. No. | $R^1$ | $R^2$ | $R^3$ | $R^4$ | X | A | B | l | m | n |
|---|---|---|---|---|---|---|---|---|---|---|
| 7. | H | -2-t-$C_4H_9$ | $-CH_3$ | $-CH_3$ | O | $-CH-$ | $-N-$ | 1 | 1 | 1 |
| 8. | H | -2-i-$C_3H_7$ | $-CH_3$ | $-CH_3$ | O | $-CH-$ | $-N-$ | 1 | 1 | 1 |
| 9. | H | -2-$CH_3$ | $-CH_3$ | $-CH_3$ | O | $-CH-$ | $-N-$ | 1 | 1 | 1 |
| 10. | H | | $-CH_3$ | $-CH_3$ | O | $-CH-$ | $-N-$ | 1 | 0 | 1 |
| 11. | H | -2-$C_6H_5$ | $-CH_3$ | $-CH_3$ | O | $-CH-$ | $-N-$ | 1 | 1 | 1 |
| 12. | H | -4-$CH_3$ | $-CH_3$ | $-CH_3$ | O | $-CH-$ | $-N-$ | 1 | 1 | 1 |
| 13. | H | -2-$CH_3$-5-i-$C_3H_7$ | $-CH_3$ | $-CH_3$ | O | $-CH-$ | $-N-$ | 1 | 2 | 1 |
| 14. | H | -5-$CH_3$-2-i-$C_3H_7$ | $-CH_3$ | $-CH_3$ | O | $-CH-$ | $-N-$ | 1 | 2 | 1 |
| 15. | H | (adamantyl) | $-CH_3$ | $-CH_3$ | O | $-CH-$ | $-N-$ | 1 | 3 | 1 |
| 16. | H | -3-i-$C_3H_7$ | $-CH_3$ | $-CH_3$ | O | $-CH-$ | $-N-$ | 1 | 1 | 1 |
| 17. | H | -2-$C_6H_{11}$ | $-CH_3$ | $-CH_3$ | O | $-CH-$ | $-N-$ | 1 | 1 | 1 |
| 18. | H | -2,4-$(CH_3)_2$ | $-CH_3$ | $-CH_3$ | O | $-CH-$ | $-N-$ | 1 | 2 | 1 |
| 19. | H | -2,6-$(CH_3)_2$ | $-CH_3$ | $-CH_3$ | O | $-CH-$ | $-N-$ | 1 | 2 | 1 |
| 20. | H | | $-CH_3$ | $-CH_3$ | O | $-CH-$ | $-N-$ | 1 | 0 | 3 |
| 21. | H | | $-CH_3$ | $-CH_3$ | O | $-CH-$ | $-N-$ | 1 | 0 | 2 |
| 22. | H | | $-CH_3$ | $-CH_3$ | O | $-CH-$ | $-N-$ | 1 | 0 | 7 |
| 23. | H | -3,3,5-$(CH_3)_3$ | $-CH_3$ | $-CH_3$ | O | $-CH-$ | $-N-$ | 1 | 3 | 1 |
| 24. | H | -4-t-$C_4H_9$ | $-Cl$ | $-OCH_3$ | O | $-CH-$ | $-N-$ | 1 | 1 | 1 |
| 25. | H | -4-t-$C_4H_9$ | $-OCH_3$ | $-OCH_3$ | O | $-N-$ | $-N-$ | 1 | 1 | 1 |
| 26. | H | -4-t-$C_4H_9$ | $-H$ | $-H$ | O | $-CCF_3$ | $-CH-$ | 1 | 1 | 1 |
| 27. | H | | $-CH_3$ | $-CH_3$ | O | $-CH-$ | $-N-$ | 1 | 0 | 5 |
| 28. | H | -3,3,5,5-$(CH_3)_4$ | $-CH_3$ | $-CH_3$ | O | $-CH-$ | $-N-$ | 1 | 4 | 1 |
| 29. | H | -3,4-$(CH_2)_4-$ | $-CH_3$ | $-CH_3$ | O | $-CH-$ | $-N-$ | 1 | 2 | 1 |
| 30. | H | -4-t-$C_4H_9$ | $-CH_3$ | $-CH_3$ | a-$CH_2$ | $-CH-$ | $-N-$ | 1 | 1 | 1 |
| 31. | H | -4-t-$C_4H_9$ | $-CH_3$ | $-CH_3$ | e-$CH_2$ | $-CH-$ | $-N-$ | 1 | 1 | 1 |
| 32. | H | -4-t-$C_5H_{11}$ | $-CH_3$ | $-OCH_3$ | O | $-CH-$ | $-N-$ | 1 | 1 | 1 |
| 33. | H | -4-i-$C_3H_7$ | $-OCH_3$ | $-OCH_3$ | O | $-CH-$ | $-N-$ | 1 | 1 | 1 |
| 34. | H | -4-$CH_3$ | $-OCH_3$ | $-OCH_3$ | O | $-CH-$ | $-N-$ | 1 | 1 | 1 |
| 35. | H | -4-$C_6H_5$ | $-OCH_3$ | $-OCH_3$ | O | $-CH-$ | $-N-$ | 1 | 1 | 1 |
| 36. | H | -4,4-$(CH_2)_5$ | $-OCH_3$ | $-OCH_3$ | O | $-CH-$ | $-N-$ | 1 | 2 | 1 |
| 37. | H | -4,4-$(CH_2)_5$ | $-CH_3$ | $-CH_3$ | O | $-CH-$ | $-N-$ | 1 | 2 | 1 |
| 38. | H | -4-t-$C_4H_9$ | $-OH$ | $-CH_3$ | O | $-C(n-C_4H_9)-$ | $-N-$ | 1 | 1 | 1 |
| 39. | H | -4-t-$C_5H_{11}$ | $-OH$ | $-CH_3$ | O | $-C(n-C_4H_9)-$ | $-N-$ | 1 | 1 | 1 |
| 40. | H | -4-t-$C_5H_{11}$ | -n-$C_5H_{11}$ | $-CH_3$ | O | $-CH-$ | $-N-$ | 1 | 1 | 1 |
| 41. | H | -4-t-$C_4H_9$ | -n-$C_5H_{11}$ | $-CH_3$ | O | $-CH-$ | $-N-$ | 1 | 1 | 1 |
| 42. | H | -4-t-$C_4H_9$ | -s-$C_4H_9$ | $-CH_3$ | O | $-CH-$ | $-N-$ | 1 | 1 | 1 |
| 43. | H | -4-t-$C_5H_{11}$ | -s-$C_4H_9$ | $-CH_3$ | O | $-CH-$ | $-N-$ | 1 | 1 | 1 |
| 44. | H | -4-t-$C_4H_9$ | -t-$C_4H_9$ | -t-$C_4H_9$ | O | $-CH-$ | $-N-$ | 1 | 1 | 1 |
| 45. | H | -4-t-$C_5H_{11}$ | -t-$C_4H_9$ | -t-$C_4H_9$ | O | $-CH-$ | $-N-$ | 1 | 1 | 1 |
| 46. | H | -4-t-$C_4H_9$ | $-CF_3$ | $-C_6H_5$ | O | $-CH-$ | $-N-$ | 1 | 1 | 1 |
| 47. | H | -4-t-$C_5H_{11}$ | $-CF_3$ | $-C_6H_5$ | O | $-CH-$ | $-N-$ | 1 | 1 | 1 |
| 48. | H | -4-t-$C_4H_9$ | $-CH_3$ | $-C_6H_5$ | O | $-CH-$ | $-N-$ | 1 | 1 | 1 |
| 49. | H | -4-t-$C_5H_{11}$ | $-CH_3$ | $-C_6H_5$ | O | $-CH-$ | $-N-$ | 1 | 1 | 1 |
| 50. | H | -4-t-$C_4H_9$ | $-H$ | $-H$ | O | $-CH-$ | $-N-$ | 1 | 1 | 1 |
| 51. | H | -4-t-$C_5H_{11}$ | $-H$ | $-H$ | O | $-CH-$ | $-N-$ | 1 | 1 | 1 |
| 52. | H | -4-t-$C_5H_{11}$ | $-H$ | $-CH_3$ | O | $-CH-$ | $-N-$ | 1 | 1 | 1 |
| 53. | H | -4-t-$C_4H_9$ | $-H$ | $-CH_3$ | O | $-CH-$ | $-N-$ | 1 | 1 | 1 |
| 54. | $CH_3$ | -4-t-$C_4H_9$ | $-CH_3$ | $-CH_3$ | O | $-CH-$ | $-N-$ | 1 | 1 | 1 |
| 55. | $CH_3$ | -4-t-$C_5H_{11}$ | $-CH_3$ | $-CH_3$ | O | $-CH-$ | $-N-$ | 1 | 1 | 1 |

Physical data for the above compounds are set out in Table II, III and IV below.

TABLE II

| Ex. No. | Analysis (%) | | | | | |
|---|---|---|---|---|---|---|
| | C | | H | | N | |
| | Calc. | Found | Calc. | Found | Calc. | Found |
| 2 | 62.44 | 62.75 | 8.55 | 8.42 | 11.50 | 10.79 |
| 15 | 69.20 | 70.14 | 8.26 | 8.29 | 12.75 | 12.32 |

TABLE II-continued

| Ex. No. | Analysis (%) | | | | | |
|---|---|---|---|---|---|---|
| | C | | H | | N | |
| | Calc. | Found | Calc. | Found | Calc. | Found |
| 16 | 70.30 | 69.56 | 9.50 | 9.44 | 13.66 | 11.79 |
| 17 | 70.15 | 70.17 | 9.25 | 9.31 | 11.68 | 11.72 |
| 18 | 66.80 | 67.27 | 8.91 | 8.96 | 13.75 | 13.49 |
| 20 | 66.80 | 67.19 | 8.91 | 9.25 | 13.75 | 13.06 |
| 21 | 65.94 | 66.35 | 8.64 | 8.69 | 14.42 | 14.21 |
| 22 | 69.76 | 70.25 | 9.75 | 10.05 | 11.62 | 11.39 |
| 23 | 67.67 | 67.69 | 9.15 | 9.62 | 13.15 | 13.09 |
| 29 | 68.84 | 68.85 | 8.81 | 9.48 | 12.67 | 12.12 |
| 32 | 63.29 | 62.77 | 8.78 | 8.54 | 11.07 | 10.17 |
| 33 | 60.52 | 60.91 | 8.32 | 8.11 | 11.95 | 10.87 |
| 38 | 67.48 | 67.23 | 9.53 | 9.79 | 10.73 | 11.01 |
| 39 | 68.11 | 67.82 | 9.69 | 10.04 | 10.36 | 10.41 |
| 40 | 71.42 | 71.20 | 10.24 | 10.33 | 10.41 | 10.55 |
| 41 | 70.91 | 70.97 | 10.09 | 10.62 | 10.79 | 10.84 |
| 42 | 70.36 | 70.82 | 9.92 | 9.96 | 11.19 | 10.84 |
| 43 | 70.91 | 70.97 | 10.09 | 9.79 | 10.79 | 10.71 |
| 44 | 71.90 | 71.86 | 10.38 | 10.79 | 10.06 | 9.72 |
| 45 | 72.34 | 72.71 | 10.51 | 9.96 | 9.73 | 9.41 |
| 46 | 64.13 | 62.19 | 6.73 | 6.97 | 9.35 | 8.18 |
| 48 | 72.88 | 71.73 | 8.41 | 8.71 | 10.62 | 10.74 |
| 49 | 73.41 | 73.07 | 8.61 | 9.07 | 10.26 | 10.27 |
| 54 | 69.12 | 68.41 | 9.57 | 9.86 | 12.09 | 12.45 |
| 55 | 69.76 | 68.49 | 9.75 | 10.09 | 11.62 | 11.50 |

TABLE III

Melting point (°C.)

| Ex. No. | | Ex. No. | |
|---|---|---|---|
| 1 | 89–112 | 32 | 90–112 |
| 3 | 66–73 | 33 | 85–110 |
| 4 | 99–108 | 34 | 110–118 |
| 14 | 43–52 | 35 | 95–115 |
| 15 | 93–96 | 36 | 105–107 |
| 22 | 80–85 | 37 | 95–97 |
| 24 | 83–101 | 47 | 105–115 |
| 25 | 119–128 | 48 | 100–105 |
| 26 | 64–80 | 49 | 120–131 |
| 28 | 60–65 | | |

TABLE IV

Molecular weight (determined by mass spectrometry)

| Ex. No. | Calc. | Found |
|---|---|---|
| 3 | 319 | 319 |
| 4 | 353 | 353 |
| 5 | 305 | 305 |
| 6 | 347 | 347 |
| 7 | 333 | 333 |
| 8 | 307 | 307 |
| 9 | 291 | 291 |
| 10 | 277 | 277 |
| 11 | 353 | 353 |
| 12 | 291 | 291 |
| 13 | 321 | 321 |
| 14 | 321 | 321 |
| 16 | 307 | 307 |
| 18 | 305 | 305 |
| 19 | 305 | 305 |
| 20 | 305 | 305 |
| 21 | 291 | 291 |
| 22 | 361 | 361 |
| 23 | 319 | 319 |
| 24 | 369 | 369 |
| 25 | 366 | 366 |
| 26 | 372 | 372 |
| 27 | 333 | 333 |
| 30 | 331 | 331 |
| 31 | 331 | 331 |
| 40 | 403 | 403 |
| 41 | 389 | 389 |
| 42 | 375 | 375 |
| 43 | 389 | 389 |
| 46 | 449 | 449 |
| 47 | 463 | 463 |
| 48 | 395 | 395 |
| 49 | 409 | 409 |
| 50 | 305 | 305 |
| 51 | 319 | 319 |
| 52 | 333 | 333 |
| 53 | 319 | 319 |
| 54 | 347 | 347 |
| 55 | 361 | 361 |

Fungicidal activity

The fungicidal activity of compounds of the invention was investigated by means of the following tests.

(a) Antisporulant activity against vine downy mildew (*Plasmopara viticola*; PVA)

The test is a direct antisporulant one using a foliar spray. The lower surfaces of leaves of whole vine plants (cv Gabernet Sauvignon), approximately 8 cm high, are inoculated by spraying with an aqueous suspension containing $5 \times 10^4$ sporangia/ml. The inoculated plants are kept for 24 hours at 21° C. in a high humidity compartment, then 24 hours at glasshouse ambient temperature and humidity. Infected leaves are sprayed on their lower surfaces with a solution of active material in 1:1 water/acetone containing 0.04% "TWEEN 20" (Trade Mark; a polyoxyethylene sorbitan ester surfactant). Plants are treated using an automated sprayline with an atomising nozzle. The concentration of the compound is 600 ppm, and the spray volume is 750 l/ha. After spraying, the plants are returned to normal glasshouse conditions for 96 hours and are then transferred to the high humidity compartment for 24 hours to induce sporulation. Assessment is based on the percentage of the leaf area covered by sporulation compared with that on control leaves.

(b) Direct protectant activity against broad bean grey mould (*Botrytis cinerea*; BCB)

The test is a direct protectant foliar spray. The upper surfaces of leaves of broad bean plants with two leaf pairs (cv The Sutton) are sprayed with the test compound at a dosage of 600 ppm using an automated sprayline as described under (a). 24 hours after spraying the leaves are inoculated with an aqueous suspension containing $10^6$ conidia/ml. For 4 days after inoculation plants are kept in a high humidity compartment at 22° C. Disease is assessed 4 days after inoculation, based on the percentage of leaf surface area covered by lesions.

(c) Activity against wheat leafspot (*Leptosphaeria nodorum*; LN.)

The test is a direct therapeutic foliar spray. Leaves of wheat plants (cv Norman), at the single leaf stage, are inoculated by spraying with an aqueous suspension containing $1.5 \times 10^6$ conidia/ml. The inoculated plants are kept for 24 hours in a high humidity compartment prior to treatment. The plants are sprayed with a solution of the test compound at a dosage of 600 ppm using an automated sprayline as described under (a). After drying, the plants are kept for 6–8 days at 22° C. and moderate humidity (70%). Assessment is based on the density of lesions per leaf compared with that on leaves of control plants.

(d) Activity against barley powdery mildew (*Erysiphe graminis f.sp. hordei*; EG)

The test is a direct therapeutic foliar spray. Leaves of barley seedlings, (cv. Golden Promise) at the single leaf stage are inoculated by dusting with mildew conidia one day prior to treatment with the test compound. The inoculated plants are kept overnight at glasshouse ambient temperature (18° C.) and humidity (40%) prior to treatment. The plants are sprayed with the test compound at a dosage of 600 ppm using an automated sprayline as described under (a). After drying, plants are returned to a compartment at 18° C. and 40% humidity for up to 7 days. Assessment is based on the percentage of leaf area covered by sporulation compared with that on leaves of control plants.

(e) Activity against rice leaf blast (*Pyricularia oryzae*; PO)

The test is a direct therapeutic foliar spray. The leaves of rice seedlings (cv Aichiaishi—about 30 seedlings per pot) at the stage of the second leaf beginning to bend are sprayed with an aqueous suspension containing $10^5$ spores/ml 24 hours prior to treatment with the test compound. The inoculated plants are kept overnight in high humidity and then allowed to dry before spraying with the test compound at a dosage of 600 ppm using an automated sprayline as described under (a). After treatment the plants are kept in a rice compartment at 25°–30° C. and high humidity. Assessments are made 4–5 days after treatment and are based on the density of necrotic lesions per leaf when compared with control plants.

(f) Activity against tomato early blight (*Alternaria solani*; AS)

This test measures the contact prophylactic activity of test compounds applied as a foliar spray. Tomato seedlings (cv Outdoor Girl) are grown to the stage at which the second true leaf is expanded. The plants are treated using an automated sprayline as described under (a). Test compounds are applied as solutions or suspensions in a mixture of acetone and water (50:50 v/v) containing 0.04% surfactant ("TWEEN 20" —Trade Mark). One day after treatment the seedlings are inoculated by spraying the leaf upper surfaces with a suspension of *A. solani* conidia containing $10^4$ spores/ml. For 4 days after inoculation plants are kept moist in a humidity compartment at 21° C. Disease is assessed 4 days after inoculation, based on the percentage of leaf surface area covered by lesions.

(g) Activity against wheat eyespot in-vitro (*Pseudocercosporella herpotrichoides*; PH)

This test measures the in vitro activity of compounds against the fungus causing wheat eyespot. The test compound is dissolved or suspended in acetone and is added into 4 ml aliquots of half strength Potato Dextrose Broth (PDB) dispensed in 25-compartment petri dishes to give a final concentration of 10 ppm compound and 3.5% acetone. The fungal inoculum consists of mycelial fragments of *P. herpotrichoides* grown in half strength PDB in shaken flasks and added to the broth to provide $5\times10^4$ fragments/ml broth. Petri dishes are incubated at 20° C. for 10 days until the assessment of mycelial growth.

(h) Activity against apple scab in-vitro (*Venturia inaequalis*: VI)

This test measures the in-vitro activity of compounds against *V. inaequalis* that causes apple scab. The test compound in acetone is added into 4 ml aliquots of half strength Potato Dextrose Broth dispensed in 25-compartment petri dishes to give final concentrations of 10 ppm. The fungal inoculum consists of mycelial fragments and spores of *V. inaequalis* grown on malt agar and added to the broth to provide $5\times10^4$ propagules/ml broth. Petri dishes are incubated at 20° C. for 10 days until the assessment of myceltal growth.

The extent of disease control in all the above tests is expressed as a rating compared with either an untreated control or a diluent-sprayed-control, according to the criteria:

0=less than 50% disease control
1=about 50–80% disease control
2=greater than 80% disease control The results of the tests are set out in Table V below.

TABLE V

| Comp. | PIP | BCB | LN | EG | PO | AS | PH | VI |
|---|---|---|---|---|---|---|---|---|
| 1 | 0 | 0 | 0 | 2 | 0 | 1 | 0 | 0 |
| 2 | 0 | 0 | 0 | 2 | 0 | 1 | 0 | 1 |
| 3 | 0 | 0 | 0 | 2 | 0 | 0 | 0 | 1 |
| 4 | 0 | 0 | 0 | 2 | 0 | 0 | 0 | 1 |
| 5 | 0 | 0 | 0 | 2 | 0 | 0 | 0 | 1 |
| 6 | 0 | 2 | 0 | 2 | 0 | 1 | 0 | 2 |
| 7 | 0 | 0 | 0 | 0 | 0 | 1 | 0 | 0 |
| 8 | 0 | 0 | 0 | 0 | 0 | 0 | 0 | 1 |
| 9 | 0 | 0 | 0 | 0 | 0 | 0 | 0 | 1 |
| 10 | 0 | 0 | 0 | 0 | 0 | 1 | 0 | 1 |
| 11 | 0 | 0 | 0 | 0 | 0 | 0 | 0 | 1 |
| 12 | 0 | 0 | 0 | 1 | 0 | 0 | 0 | 1 |
| 13 | 0 | 0 | 0 | 1 | 0 | 0 | 0 | 1 |
| 14 | 0 | 0 | 0 | 0 | 0 | 0 | 0 | 1 |
| 15 | 0 | 0 | 0 | 0 | 0 | 0 | 0 | 1 |
| 16 | 1 | 0 | 0 | 2 | 0 | 0 | 1 | 1 |
| 17 | 0 | 0 | 0 | 0 | 0 | 0 | 0 | 1 |
| 18 | 0 | 0 | 0 | 1 | 0 | 0 | 0 | 1 |
| 19 | 2 | 0 | 0 | 0 | 0 | 0 | 0 | 0 |
| 20 | 0 | 2 | 0 | 0 | 0 | 0 | 2 | 2 |
| 21 | 0 | 0 | 0 | 0 | 0 | 0 | 1 | 1 |
| 22 | 0 | 0 | 0 | 0 | 0 | 0 | 0 | 1 |
| 23 | 0 | 0 | 0 | 0 | 0 | 0 | 0 | 1 |
| 24 | 0 | 2 | 0 | 2 | 0 | 0 | 2 | 1 |
| 25 | 0 | 1 | 0 | 2 | 0 | 0 | 0 | 0 |
| 26 | 2 | 0 | 0 | 2 | 0 | 1 | 1 | 1 |
| 27 | 0 | 0 | 0 | 0 | 0 | 0 | 0 | 1 |
| 28 | 0 | 0 | 1 | 0 | 0 | 0 | 0 | 0 |
| 29 | 0 | 0 | 0 | 0 | 2 | 0 | 0 | 1 |
| 30 | 0 | 0 | 0 | 2 | 0 | 2 | 0 | 1 |
| 31 | 0 | 0 | 0 | 2 | 0 | 0 | 0 | 1 |
| 32 | 0 | 1 | 0 | 2 | 0 | 2 | 0 | 0 |
| 33 | 0 | 0 | 0 | 2 | 0 | 0 | 0 | 0 |
| 34 | 0 | 0 | 0 | 0 | 0 | 0 | 0 | 0 |
| 35 | 0 | 1 | 0 | 0 | 0 | 0 | 0 | 0 |
| 36 | 0 | 0 | 0 | 0 | 0 | 0 | 0 | 0 |
| 37 | 0 | 0 | 0 | 1 | 0 | 0 | 1 | 1 |
| 38 | 0 | 0 | 0 | 0 | 0 | 2 | 0 | 1 |
| 39 | 0 | 0 | 0 | 0 | 0 | 2 | 0 | 1 |
| 40 | 0 | 0 | 0 | 2 | 0 | 2 | 0 | 0 |
| 41 | 0 | 0 | 0 | 2 | 0 | 0 | 0 | 2 |
| 42 | 0 | 0 | 0 | 2 | 0 | 2 | 0 | 1 |
| 43 | 0 | 0 | 0 | 2 | 0 | 2 | 0 | 1 |
| 44 | 0 | 2 | 0 | 0 | 0 | 0 | 0 | 0 |
| 45 | 0 | 0 | 0 | 0 | 0 | 0 | 0 | 0 |
| 46 | 0 | 0 | 0 | 1 | 0 | 0 | 0 | 0 |
| 47 | 0 | 0 | 0 | 1 | 0 | 1 | 0 | 0 |
| 48 | 0 | 0 | 0 | 2 | 0 | 1 | 0 | 0 |
| 49 | 0 | 0 | 0 | 2 | 0 | 1 | 0 | 0 |
| 50 | 0 | 0 | 0 | 2 | 0 | 1 | 0 | 2 |
| 51 | 0 | 0 | 0 | 2 | 0 | 1 | 0 | 2 |
| 52 | 0 | 0 | 0 | 2 | 0 | 2 | 0 | 2 |
| 53 | 0 | 0 | 0 | 2 | 0 | 1 | 0 | 2 |
| 54 | 0 | 0 | 0 | 2 | 0 | 0 | 0 | 0 |
| 55 | 0 | 0 | 0 | 2 | 0 | 0 | 0 | 0 |

I claim:
1. A method of combating fungi at a locus which comprises treating the locus with a fungicidally effective amount of a compound of the formula I:

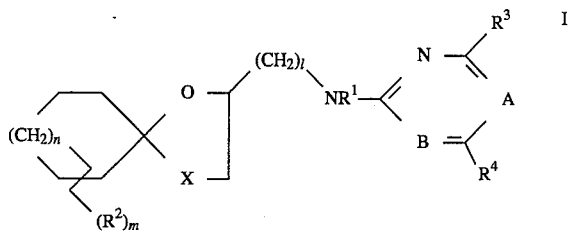

or an acid-addition salt thereof
in which
X represents O or $CH_2$,
$R^1$ represnts a hydrogen atom or an optionally substituted alkyl, cycloalkyl, haloalkyl, alkenyl, alkynyl, aryl or aralkyl group,
$R^2$ represents an optionally substituted alkyl, cycloalkyl, cycloalkylalkyl, alkoxy, alkyoxyalkyl, aryl or aryloxy group, or $R^2$, together with the ring to which it is attached, represents a polycyclic hydrocarbyl group,
A represents a group $CR^5$ and B represents a nitrogen atom,
$R^3$, $R^4$ and $R^5$ each independently represent a hydrogen or halogen atom, a hydroxy or cyano group or an optionally substituted alkyl, alkenyl, alkynyl, haloalkyl, alkoxyalkyl, aralkyl, aryl, alkylamino, alkylthio or alkoxy group,
l represents an integer from 1 to 3,
m represents an integer from 1 to 6, and
n represents zero or an integer from 1 to 3.

2. A method according to claim 1, in which any alkyl, alkenyl, alkynyl part of any of the substituents $R^1$ to $R^5$ contains up to 10 carbon atoms, any cycloalkyl part of any of the substituents $R^1$ to $R^5$ contains from 3 to 8 carbon atoms, any alkylene chain contains from 1 to 8 chain members, and any aryl part of any of the substituents $R^1$ to $R^5$ contains 6 to 10 carbon atoms, and in which each optionally substituted group independently is substituted by one or more halogen atoms or nitro, cyano, $C_{1-6}$ alkyl, $C_{3-6}$ cycloalkyl, $C_{1-6}$ haloalkyl, $C_{3-6}$ halocycloalkyl, $C_{1-6}$ alkoxy, $C_{1-6}$ haloalkoxy, optionally substituted amino, formyl, $C_{1-6}$ alkoxycarbonyl, carboxyl, phenyl or halo- or dihalo-phenyl groups.

3. A method according to claim 1, in which X represents O.

4. A method according to claim 1, in which $R^1$ represents a hydrogen atom, a $C_{1-6}$ alkyl, $C_{3-6}$ cycloalkyl, $C_{2-6}$ alkenyl, $C_{2-6}$ alkynyl, phenyl or benzyl group, each group optionally substituted by one or more halogen atoms, or $C_{1-4}$ alkyl, $C_{1-4}$ haloalkyl, $C_{1-4}$ alkoxy, $C_{1-4}$ alkylamino, $C_{1-4}$ dialkylamino or phenylamino groups.

5. A method according to claim 4, in which $R^1$ represents a hydrogen atom or a methyl or ethyl group optionally substituted by up to three chlorine or fluorine atoms, an ethenyl, propenyl or propynyl group of a phenyl or benzyl group.

6. A method according to claim 1, in which $R^2$ or each $R^2$ independently represents a $C_{1-10}$ alkyl, $C_{3-6}$ cycloalkyl, $C_{3-8}$ cycloalkyl-$C_{1-6}$ alkyl, $C_{1-6}$ alkoxy, $C_{1-10}$ alkoxy-$C_{1-6}$ alkyl or phenyl group, $R^2$ or each $R^2$ together with the ring to which they are attached, represents a $C_{7-20}$ polycyclic group, each of the above groups optionally substituted by one or more halogen atoms, or $C_{1-4}$ alkyl, $C_{1-4}$ haloalkyl or $C_{1-4}$ alkoxy groups.

7. A method according to claim 6, in which $R^2$ represents a $C_{3-8}$ alkyl group.

8. A method according to claim 1, in which $R^2$ represents a secondary butyl, tertiary butyl or tertiary amyl group attached to the 4-position of the cycloalkyl ring.

9. A method according to claim 1, in which m represents 1 or 2.

10. A method according to claim 1, in which $R^2$ is attached to the positions 3, 4 or 5 of the cycloalkyl ring.

11. A method according to claim 1, in which $R^3$, $R^4$, and $R^5$ each independently represent a hydrogen or halogen atom, or an optionally substituted $C_{1-6}$ alkyl, $C_{1-6}$ alkenyl, $C_{1-6}$ haloalkyl, benzyl, phenyl or $C_{1-6}$ alkoxy group, each group optionally substituted by one or more halogen atoms or a $C_{1-4}$ alkyl, $C_{1-4}$ haloalkyl, $C_{1-4}$ alkoxy, $C_{1-4}$ alkylamino, $C_{1-4}$ dialkylamino or phenylamino groups.

12. A method according to claim 11, in which $R^3$ and $R^4$ each independently represent a hydrogen or halogen atom, a hydroxy group or a methyl, ethyl, propyl, butyl, pentyl, hexyl, phenyl, methoxy or ethoxy group, each group optionally substituted by up to three chlorine or fluorine atoms.

13. A method according to claim 11 in which $R^5$ represents a hydrogen or halogen atom, or a methyl, ethyl, propyl, methoxy or ethoxy group, each group optionally substituted by up to three chlorine or fluorine atoms.

14. A method according to claim 1, in which l and n represent 1.

15. A method according to claim 1, wherein said locus comprises plants subject to or subjected to fungal attack, seeds of such plants or the medium in which the plants are to be grown.

16. A method according to claim 15, wherein said locus comprises cereals.

* * * * *